United States Patent
Termin et al.

(10) Patent No.: US 6,890,351 B2
(45) Date of Patent: May 10, 2005

(54) METHOD FOR TREATING DISEASED OR DAMAGED ORGANS

(75) Inventors: Paul L. Termin, St. Paul, MN (US); Robert M. Carr, Jr., West Roxbury, MA (US); Kimberlie D. Condon, Brant Rock, MA (US)

(73) Assignee: Organogenesis Inc., Canton, MA (US)

( * ) Notice: Subject to any disclaimer, the term of this patent is extended or adjusted under 35 U.S.C. 154(b) by 0 days.

(21) Appl. No.: 09/949,043

(22) Filed: Sep. 7, 2001

(65) Prior Publication Data

US 2002/0019663 A1 Feb. 14, 2002

Related U.S. Application Data

(63) Continuation of application No. 08/889,079, filed on Jul. 7, 1997, now Pat. No. 6,334,872, which is a continuation-in-part of application No. 08/461,756, filed on Jun. 5, 1995, now abandoned, which is a continuation of application No. 08/198,062, filed on Feb. 18, 1994, now abandoned.

(51) Int. Cl.[7] ................................................. A61F 2/06
(52) U.S. Cl. ........................ 623/1.38; 623/1.1; 623/1.47; 623/917
(58) Field of Search ................................ 623/1.1, 1.38, 623/1.44, 1.47, 23.72, 23.75, 917, 2.13, 916, 23.64, 23.65

(56) References Cited

U.S. PATENT DOCUMENTS

| | | | |
|---|---|---|---|
| 2,127,903 A | | 8/1938 | Bowen |
| 3,272,204 A | * | 9/1966 | Artandi et al. .............. 128/334 |
| 3,329,572 A | | 7/1967 | Malgouzou |
| 3,551,560 A | | 12/1970 | Thiele |
| 3,562,820 A | * | 2/1971 | Braun ............................... 3/1 |
| 3,914,802 A | | 10/1975 | Relck |
| 3,919,411 A | | 11/1975 | Glass et al. |
| 3,974,526 A | | 8/1976 | Dardik et al. |
| 4,082,507 A | | 4/1978 | Sawyer ............................. 8/94 |
| 4,148,664 A | | 4/1979 | Cruz, Jr. |
| 4,252,759 A | | 2/1981 | Yannas et al. ................ 264/86 |
| 4,319,363 A | | 3/1982 | Ketharanathan ................ 3/1.4 |
| 4,323,525 A | | 4/1982 | Bornat |

(Continued)

FOREIGN PATENT DOCUMENTS

| | | |
|---|---|---|
| DE | 1694509 | 6/1971 |
| EP | 0 397 500 A2 | 11/1990 |
| EP | 0 493 788 A1 | 7/1992 |

(Continued)

OTHER PUBLICATIONS

Matsumoto, T. et al.; (1966),The Fate of the Inverted Segment of Small Bowel Used for the Replacement of Major Veins; Surgery, vol. 60 (3), pp. 739–743.

Fraser, R.E. et al.; (1968); Experimental Replacement of the Superior Vena Cava; Arch. Surg. vol. 96, pp. 378–385.

Egusa, S.; (1968); Experimental Study on Vascular Graft II. Replacement of Inferior Vena Cava and Abdominal Aorta with the Autogenous Segment of Samll Intestinal Submucosal; Acta Med. Okayama 22, pp. 153–165.

(Continued)

*Primary Examiner*—Bruce Snow
*Assistant Examiner*—Cheryl Miller
(74) *Attorney, Agent, or Firm*—Wilmer Cutler Pickering Hale and Dorr LLP

(57) ABSTRACT

A bioremodelable prosthesis for treating a patient with a diseased or damaged organs comprising a first layer that contains acid-extracted fibrillar or non-fibrillar collagen, and a second layer derived from the tunica submucosa of the small intestine that provides structural stability, is pliable and is semi-permeable,pe1 59564443.npc wherein the prosthesis undergoes controlled biodegradation occurring with adequate living cell replacement such that the original prosthesis is replaced by the patient's living cells.

22 Claims, 9 Drawing Sheets

INNER ICL
OUTER DFC

DFC/ICL/DFC

INNER DFC-
OUTER ICL

U.S. PATENT DOCUMENTS

| Patent | Date | Inventor | |
|---|---|---|---|
| 4,378,224 A | 3/1983 | Nimni et al. | 8/94 |
| 4,420,339 A | 12/1983 | Kato | |
| 4,475,972 A | 10/1984 | Wong | |
| 4,502,159 A | 3/1985 | Woodroof et al. | 3/1.4 |
| 4,539,716 A | 9/1985 | Bell | 623/1 |
| 4,597,762 A | 7/1986 | Walter et al. | |
| 4,629,458 A | 12/1986 | Pinchuk | |
| 4,703,108 A | 10/1987 | Silver et al. | |
| 4,755,593 A | 7/1988 | Lauren | |
| 4,787,900 A * | 11/1988 | Yannas | 623/1 |
| 4,801,299 A | 1/1989 | Brendel et al. | 623/1 |
| 4,814,120 A | 3/1989 | Huc et al. | 264/28 |
| 4,822,361 A | 4/1989 | Okita et al. | 623/12 |
| 4,842,575 A | 6/1989 | Hoffman, Jr. et al. | 600/36 |
| 4,863,666 A | 9/1989 | Griffiths et al. | |
| 4,863,668 A | 9/1989 | Griffiths et al. | |
| 4,889,120 A | 12/1989 | Gordon | |
| 4,902,289 A | 2/1990 | Yannas | 623/1 |
| 4,902,290 A | 2/1990 | Fleckenstein et al. | 623/1 |
| 4,902,508 A * | 2/1990 | Badylak et al. | 424/95 |
| 4,923,380 A | 5/1990 | Huc et al. | |
| 4,956,178 A | 9/1990 | Badylak et al. | 424/551 |
| 5,002,583 A | 3/1991 | Pitaru et al. | |
| 5,007,934 A | 4/1991 | Stone | |
| 5,024,671 A | 6/1991 | Tu et al. | 623/1 |
| 5,026,381 A * | 6/1991 | Li | 606/152 |
| 5,026,695 A | 7/1991 | Eckmayer | |
| 5,028,695 A | 7/1991 | Eckmayer et al. | |
| 5,037,377 A | 8/1991 | Alonso | 600/36 |
| 5,061,276 A | 10/1991 | Tu et al. | 623/1 |
| 5,084,065 A | 1/1992 | Weldon et al. | |
| 5,106,949 A | 4/1992 | Kemp et al. | 530/356 |
| 5,108,424 A | 4/1992 | Hoffman, Jr. et al. | 623/1 |
| 5,131,908 A | 7/1992 | Dardik et al. | |
| 5,131,977 A | 7/1992 | Dardik et al. | |
| 5,197,977 A | 3/1993 | Hoffman, Jr. et al. | |
| 5,219,576 A | 6/1993 | Chu et al. | |
| 5,256,418 A | 10/1993 | Kemp et al. | 424/423 |
| 5,263,983 A | 11/1993 | Yoshizato et al. | 623/12 |
| 5,263,984 A | 11/1993 | Li et al. | |
| 5,266,480 A | 11/1993 | Naughton et al. | |
| 5,281,422 A * | 1/1994 | Badylak et al. | 424/551 |
| 5,336,616 A | 8/1994 | Livesey et al. | |
| 5,372,821 A | 12/1994 | Badylak | |
| 5,374,515 A | 12/1994 | Parenteau et al. | 435/1 |
| 5,376,110 A | 12/1994 | Tu et al. | 623/1 |
| 5,376,376 A * | 12/1994 | Li | 424/443 |
| 5,378,469 A | 1/1995 | Kemp et al. | 424/423 |
| 5,413,597 A | 5/1995 | Krajicek | 623/1 |
| 5,445,833 A | 8/1995 | Badylak et al. | |
| 5,460,962 A | 10/1995 | Kemp | |
| 5,480,424 A | 1/1996 | Cox | |
| 5,487,895 A | 1/1996 | Dapper et al. | |
| 5,523,291 A * | 6/1996 | Janzen et al. | 514/21 |
| 5,554,389 A | 9/1996 | Badylak et al. | |
| 5,567,806 A | 10/1996 | Abdul-Malak et al. | |
| 5,571,216 A | 11/1996 | Anderson | |
| 5,573,784 A | 11/1996 | Badylak et al. | |
| 5,618,718 A | 4/1997 | Auger et al. | |
| 5,624,840 A | 4/1997 | Naughton et al. | |
| 5,645,860 A | 7/1997 | Knapp, Jr. et al. | |
| 5,667,961 A | 9/1997 | Bernard et al. | |
| 5,711,969 A | 1/1998 | Patel et al. | |
| 5,713,950 A | 2/1998 | Cox | |
| 5,716,404 A | 2/1998 | Vacanti et al. | |
| 5,733,337 A | 3/1998 | Carr, Jr. et al. | |
| 5,753,267 A | 5/1998 | Badylak et al. | |
| 5,755,791 A | 5/1998 | Whitson et al. | |
| 5,762,966 A | 6/1998 | Knapp, Jr. et al. | |
| 5,776,182 A | 7/1998 | Bruchman et al. | |
| 5,778,625 A | 7/1998 | Plouhar et al. | |
| 5,800,537 A | 9/1998 | Bell | |
| 5,824,063 A | 10/1998 | Cox | |
| 5,851,230 A | 12/1998 | Weadock et al. | |
| 5,866,414 A | 2/1999 | Badylak et al. | |
| 5,879,383 A | 3/1999 | Bruchman et al. | |
| 5,885,619 A | 3/1999 | Patel et al. | |
| 5,893,888 A | 4/1999 | Bell | |
| 5,922,028 A | 7/1999 | Plouhar et al. | |
| 5,948,654 A | 9/1999 | Tranquillo et al. | |
| 5,955,110 A | 9/1999 | Patel et al. | |
| 5,968,092 A | 10/1999 | Buscemi et al. | |
| 5,968,096 A | 10/1999 | Whitson et al. | |
| 5,993,844 A * | 11/1999 | Abraham et al. | 424/423 |
| 5,997,575 A | 12/1999 | Whitson et al. | |
| 6,090,995 A | 7/2000 | Reich et al. | |
| 6,096,347 A | 8/2000 | Geddes et al. | |
| 6,099,567 A | 8/2000 | Badylak et al. | |
| 6,126,686 A | 10/2000 | Badylak et al. | |
| 6,176,880 B1 | 1/2001 | Plouhar et al. | |
| 6,187,039 B1 | 2/2001 | Hiles et al. | |
| 6,206,931 B1 | 3/2001 | Cook et al. | |
| 6,241,981 B1 | 6/2001 | Cobb et al. | |
| 6,334,872 B1 | 1/2002 | Termin et al. | |
| 6,572,650 B1 | 6/2003 | Abraham et al. | |
| 6,599,690 B1 | 7/2003 | Abraham et al. | |

FOREIGN PATENT DOCUMENTS

| | | |
|---|---|---|
| EP | 493788 | 7/1992 |
| EP | 564786 | 10/1993 |
| FR | 2679778 | 2/1993 |
| GB | 2153235 A | 8/1985 |
| JP | 49-28193 | 7/1974 |
| JP | 59-177042 | 10/1984 |
| JP | 60-34450 | 2/1985 |
| JP | 01-230366 | 9/1989 |
| JP | 4-501516 | 3/1992 |
| JP | 05-344988 | 12/1993 |
| WO | WO 89/10100 | 11/1989 |
| WO | 8910100 | 11/1989 |
| WO | 93/02666 | 2/1993 |
| WO | 93/10722 | 6/1993 |
| WO | 95/22301 | 8/1995 |
| WO | 95/28283 | 10/1995 |
| WO | 96/31157 | 10/1996 |
| WO | 98/06445 | 2/1998 |
| WO | 98/10775 | 3/1998 |
| WO | 98/25543 | 6/1998 |
| WO | 98/25544 | 6/1998 |
| WO | 98/25545 | 6/1998 |
| WO | 98/25546 | 6/1998 |
| WO | 98/25637 | 6/1998 |
| WO | 98/25964 | 6/1998 |
| WO | 98/44969 | 10/1998 |
| WO | 98/49969 | 11/1998 |
| WO | 99/12555 | 3/1999 |
| WO | 99/63051 | 12/1999 |
| WO | 00/32250 | 6/2000 |
| WO | 02/22184 | 3/2002 |

OTHER PUBLICATIONS

Lawler, M.R., Jr. et al.; (1971); Evaluation of Canine Intestinal Submucosa as a Vascular Substitute; The American Journal of Surgery, vol. 122, pp. 517–519.

Dagan, R. et al., (1983); Glutaraldehyde Treated Cat Small Bowel as an Arterial Graft; Vascular Surgery, Jul./Aug., pp. 199–206.

Broll, R. et al.; (1986); Replacement of Dog's Aorta by Autologous Intestinal Muscle in the Infected Retroperitoneum; Eur. Surg. Res., vol. 18, pp. 390–396.

American National Standard for Vascular Graft Prostheses; Association for the Advancement of Medical Instrumentation, approved Jul. 7, 1986.

Hiles, M.C. et al.; (1993); Porosity of Porcine Small–Intestinal Submucosa for Use as a Vascular Graft; Journal of Biomed. Material Res., vol. 27, pp. 139–144.

Carr, R.M. et al.; (1994); The Study of the Release of Benzalkonium–Heparin Complex from an Absorbable Synthetic Colagen Graft; The 20th Annual Meeting of the Society for Biomaterials, Apr. 5–9, Boston, MA.

Haimovici, H.; Patch Graft Angioplasty; Vascular Surgery, Third Edition, pp. 287–292.

Silverman, G.J.; Sterilization and Preservation by Ionizing Irradiation; In *Disinfection, Sterilization, and Preservation,* Fourth Ed., London–Philadelphia, Lea & Febiger, Ch. 32, pp. 566–579.

Abbott, W.M. et al.; (1993) Evaluation and Performance Standards for Aterial Prostheses, Journal of Vascular Surgery, vol. 17, No. 4, pp. 746–756.

Termin, P.L. et al.; (1994); Remodeling of an Absorbable Synthetic Collagen Graft: Long Term Implant Histology, The 20th Annual Meeting of the Society for Biomaterials, Apr. 5–9, Boston, MA.

Abbott, W. M. et al., "Evaluation and Performance Standards for Arterial Prostheses", Journal of Vascular Surgery, 1993; 17:746–756.

Haimovici, Henry, "Patch Graft Angioplasty", Vascula Surgery, edition pp. 287–292.

American National Standard for Vascular Graft Protheses, by the Association for the Advancement of Medical Instrumentation, approved Jul. 7, 1986.

Lawler, Marion R. Jr., et al., Evaluation of Canine Intestinal Submucosa as a Vascular Substitute, vol. 122, pp. 517–519, Oct. 1971.

Dagan, R. M. D. et al., Glutaraldehyde Treated Cat Small Bowel as an Arterial Graft, Vascular Surgery, pp 199–206.

Egusa, Shigemi, Experimental Study on Vascular Graft II replacement of Inferior Vena Cava and Abdominal Aorta with the Autogenous Segment of Small Intestinal Submucosa, Acta Med. Okayama 22, 153–165 (1968).

Fraser, R.E., et al., Experimental Replacement of the Superior Vena Cava, Arch Surg, vol. 96, pp 378–385, Mar. 1968.

Broll, R., et al., Replacement of Dog's Aorta by Autologous Intestimal Muscle in the Infected Retroperitoneum, Eur. surg. Res. 18: 390–396 (1986).

Hiles, M.C., et al., Purosity of porcine small–intesetinal submucosa for use as a vascular graft, Journal of Biomedical Materials Research, vol. 27, 139–144 (1993).

Matsumoto, Teruo, et al., The fate of the inverted segment of the small bowel used for the replacement of major veins, Surgery, Sep. 1966, vol. 60, No. 3, pp 739–743.

Angelini G.D., et al., "External Stenting Reduces Early Medial and Neointimal Thickening in a Pig Model of Arteriovenous Bypass Grafting", J Thor Cardiovasc Surg., vol. 112, No. 1 (1996).

Barra J.A., et al., "Constrictive Perivenous Mesh Prosthesis for Preservation of Vein Integrity", J. Thorac. Cardiovasc Surg., 92:330–336 (1986).

Batellier J, et al., "Protection from Atherosclerosis In Vein Grafts by a Rigid External Support", Arteriosel Thromb., 13(3): 379–384 (1993).

Bateman J.F. et al., "Induction of Procollagen Processing in Fibroblast Cultures by Neutral Polymers", Journal of Biological Chemistry, 261(9):4198–4203 (1986).

Cobb M.A. et al., "Histology After Dural Grafting with Small Intestinal Submucosa", Surg Neurol, 46:389–394 (1996).

Davies M.G., et al., "Reduction of Experimental Vein Graft Intimal Hyperplasia and Preservation of Nitric Oxide–Mediated Relaxation by the Nitric Oxide Precursos L–arginine", Surgery, 116(3): 557–568 (1994).

Dobrin P.B., et al., "Mechanical Factors Predisposing to Intimal Hyperplasia and Medial Thichening in Autogenous Vein Grafts", Surgery 105(3): 393–400 (1989).

Fillinger MF, et al., "Vein Adaptation to the Hemodynamic Environment of Infrainguinal Grafts", J. Vasc Surg., 19(6): 970–979 (1994).

Fleischmajer R. et al., "Imunochemistry of a Keratinocyte–Fibroblast Co–culture Model for Reconstruction of Human Skin", J Histochem Cytochem, 41(9): 1359–1366 (1993).

Gibbons G.H. et al., "The Emerging Concept of Vascular Remodeling", NEJM, 330(20): 1431–1438 (1994).

Golledge, J., et al. "Circumferential Deformation and Shear Stress Induce Differential Responses in Saphenous Vein Endothelium Exposed to Arterial Flow", J. Clin. Invest., 99(11)2719–2726 (1997).

Griffith L.G., et al., "Tissue Engineering –Current Challenges and Expanding Oppurtunities", Science 295:1009–1014 (2002).

Grinnell F., et al., "Collagen Processing, Crosslinking, and Fibril Bundle Assembly in Matrix Produced by Fibroblasts in Long–Term Cultures Supplemented with Ascorbic Acid", Experimental Cell Research, 181:483–491 (1989).

Hata R.I., et al., "L–Ascorbic Acid 2–Phosphate Stimulates Collagen Accumulation, Cell Proliferation, and Formation of a Three–Dimensional Tissuelike Substance by Skin Fibroblasts", Journal of Cellular Physiology, 138:8–16 (1989).

Huynh T.T., et al., "Local Inhibition of Tyrosine Kinase Activity Markedly Attenuates the Development of Intimal Hyperplasia in Experimental Vein Grafts", J Surg. Res., 77:104–111 (1998).

Kohler T.R., et al., "The Effect of Rigid External Support on Vein Graft Adaptation to the Arterial Circulation", J Vasc Surg., 9(2): 277–285 (1989).

Krippaehne W.W., et al., "Effects of Function on Grafts of Autologous and Homologous Connective Tissue", Surgical Forum, vol. 12, 97–99, 47th Annual Clinical Congress (1961).

Krippaehne W.W., et al., "Studies on the Effect of Stress on Transplants of Autologous and Homologous Connective Tissue", Am. J. Surg., 104:267–272 (1962).

Matsumoto, T., et al., "Further Application of Intestinal Submucosa as a Patch Graft", Surgery, vol. 61(4): 584–587 (1967).

Okadome K, et al., "Ultrastructural Evidence of the Effects of Shear Stress Variation on Intimal Thickening In Dogs with Arterially Transplanted Autologous Vein Grafts", J Cardiovasc Surg., 31:719–726 (1990).

Resnick N., et al., "Hemodynamic Forces are Complex Regulators of Endothelial Gene Expression", FASEB J., 9:874–882 (1995).

Rottholf, G. et al., "Aortic Replacement with Multi–Layer Submucosa Prostheses made from Heterologous Small Intestine", J. Cardiovas. Surg., 3:31–35.

Steven F.S. et al., "Polymeric Collagen Isolated from the Human Intestinal Submucosa", Gut, 10:484–487 (1969).

Yamamura S, et al., "Blood Flow and Kinetics of Smooth Muscle Cell Proliferation In Canine Autogenous Vein Grafts: In Vivo BrdU Incorporation", J. Surg. Res., 56:155–161 (1994).

Zweep H.P., et al., "Autologous Vein Supported With a Biodegradable Prosthesis for Arterial Grafting", Ann Thorac Surg., 55:427–433 (1993).

Abraham, Ginger, Evaluation of the Porcine Intestinal Collagen Layer as a Biomaterial.

Badylak, S., Endothelial Cell Adherence to Small Intestinal Submucosa: An Acellular Bioscaffold, Biomaterials 20, 2257–2263 (1999).

Bodnar, E., et al., Thorac. Cardiovascular Surg., 34:82–85 (1986).

Courtman, et al., J. of Biomedical Research, 28:655–666 (1994).

Dejardin, L., Use of Small Intestinal Submucosal Implants for Regeneration of Large Fascial Defects: An experimental Study in Dogs.

Dobrin, Hypertension, 26: 38–43 (1995).

Gloeckner, D., Mechanical Evaluation and Design of a Multilayered Collagenous Repair Biomaterial.

Kraiss et al., Circ. Res., 79: 45–53 (1996).

Onohara et al., J. Surg. Res., 55: 344–50 (1993).

Mehta et al., Nature Medicine, 4: 235–39 (1998).

Prevel, C., Small Intestinal Submucosa: Utilization as a Wound Dressing in Full–Thickness Rodent Wounds, Ann Plast Surg 35:381–388 (1995).

Prevel, C.D. Experimental Evaluation of Small Intestine Submucosa as a Microvascular Graft Material, Microsurgery 15:586–591 (1994).

Schwartz et al., J. Vasc. Surg. 15: 176–186 (1992).

Staros, Biochem., 21: 3950–55 (1982).

Takahashi and Berk, Journal of Clinical Investigation, 98: 2623–2631 (1996).

Wilson, G.J., et al., Ann. Thorac, Surg., 60:5353–5358 (1995).

Wyler et al., Journal of Biomedical Materials Research, 26: 1141–1146 (1992).

Zwolak et al., J. Vasc. Surg., 5: 126–36 (1987).

* cited by examiner

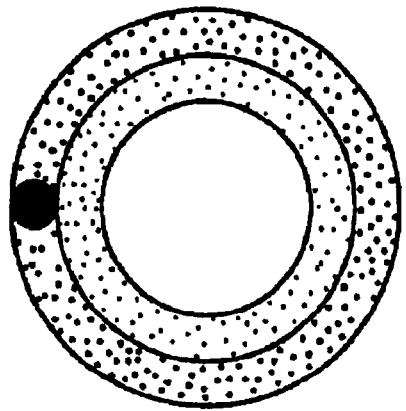
FIG.1C INNER DFC–OUTER ICL
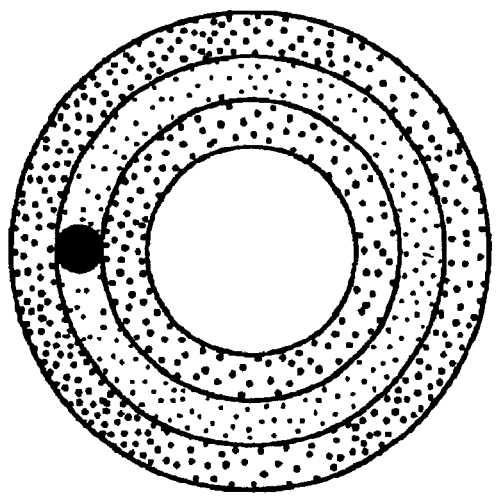
FIG.1B DFC/ICL/DFC
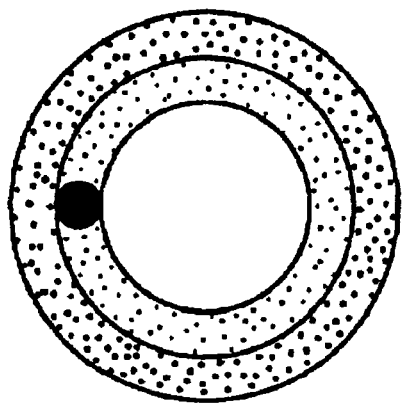
FIG.1A INNER ICL OUTER DFC

METHOD FOR TREATING DISEASED OR DAMAGED ORGANS

CROSS REFERENCE TO RELATED APPLICATIONS

This application is a continuation of U.S. patent application Ser. No. 08/889,079, filed Jul. 7, 1997 now U.S. Pat. No. 6,334,872, which is a continuation-in-part of U.S. patent application Ser. No. 08/461,756, filed Jun. 5, 1995, now abandoned, which is a continuation of U.S. patent application Ser. No. 08/198,062, filed Feb. 18, 1994, now abandoned; each of which is in its entirety hereby incorporated by reference.

FIELD OF THE INVENTION

This invention is in the field of tissue engineering. The present invention is a resilient, biocompatible two- or three-layered tissue graft which can be engineered in flat sheets or in tubes with various luminal diameters and thicknesses. At least one layer is composed of collagen or a collagenous material. The present invention is gradually degraded and bioremodeled by the host's cells which replace the implanted prosthesis and assume its shape.

BACKGROUND OF THE INVENTION

Each year approximately 300,000 coronary bypass procedures are performed in the United States. The typical treatment for small diameter artery replacement has been for surgeons to use the patient's own vessels, usually the saphenous vein from the leg. However, in many cases, the use of the patient's own vessels is not practical because the veins are either damaged, diseased or are not available. In these cases, synthetic materials are used, but with unsatisfactory long-term results. It is still a continuing goal of researchers to develop prostheses which can successfully be used to replace or repair mammalian tissue, particularly blood vessels.

SUMMARY OF THE INVENTION

This invention is directed to a method for treating damaged or injured organs, particularly blood vessels, by replacing, or repairing, a section of the organ in a patient with a bioremodelable collagen graft prostheses. This prosthesis, when implanted into a mammalian host, undergoes controlled biodegradation accompanied by adequate living cell replacement, or neo-tissue formation, such that the original implanted prosthesis is bioremodeled by the host's cells before it is digested by host enzymes. The prosthesis of this invention comprises at least two layers: (a) at least one layer is composed of collagen or a collagenous material; and (b) at least one layer is composed of material which provides structural stability, and is pliable, semi-permeable, and suturable. In the preferred embodiment of this invention, the two-layered prosthesis has an inner (luminal) layer which provides a smooth, thrombosis-resistant flow surface and an outer structural layer which provides structural stability, and is pliable, semi-permeable, and suturable. In another preferred embodiment of this invention the prosthesis has three layers: an inner (luminal) layer which acts as a smooth, thrombosis-resistant flow surface; a middle structural layer which provides structural stability, and is pliable, semi-permeable, and suturable; and, an outer (abluminal) layer. The outer layers of both the two-layer or the three-layer prosthesis add strength to the graft and allow the patient's host cells to attach and grow into the graft thereby facilitating the bioremodeling.

The invention is also directed to methods for preparing bioremodelable two- or three-layer tubular blood vessel prostheses by (a) forming a tubular structural layer that is pliable, semi-permeable, and suturable; (b) forming an inner layer to act as a smooth flow surface comprising deposition of acid-extracted fibrillar collagen onto the luminal surface of said structural layer of step (a); and, (c) creating the lumen. The inner layer may also be treated with drugs for anti-thrombotic effect, such as heparin or other appropriate agent(s). The prosthesis is next implanted into a mammalian host where it undergoes controlled biodegradation accompanied by adequate living cell replacement, or neo-tissue formation, such that the original implanted prosthesis is bioremodeled by the host's cells.

BRIEF DESCRIPTION OF THE FIGURES

FIGS. 1A, 1B and 1C are schematic cross-sectional view of the preferred prosthesis in accordance with the present invention. FIG. 1A represents a two layer prosthesis with an outer collagenous layer and an inner structural layer. FIG. 1B represents a prosthesis with three layers: inner and an outer collagenous layers and a middle structural layer. FIG. 1C represents a two layer prosthesis with an inner collagenous layer and an outer structural layer.

DETAILED DESCRIPTION OF THE INVENTION

Figure 2:
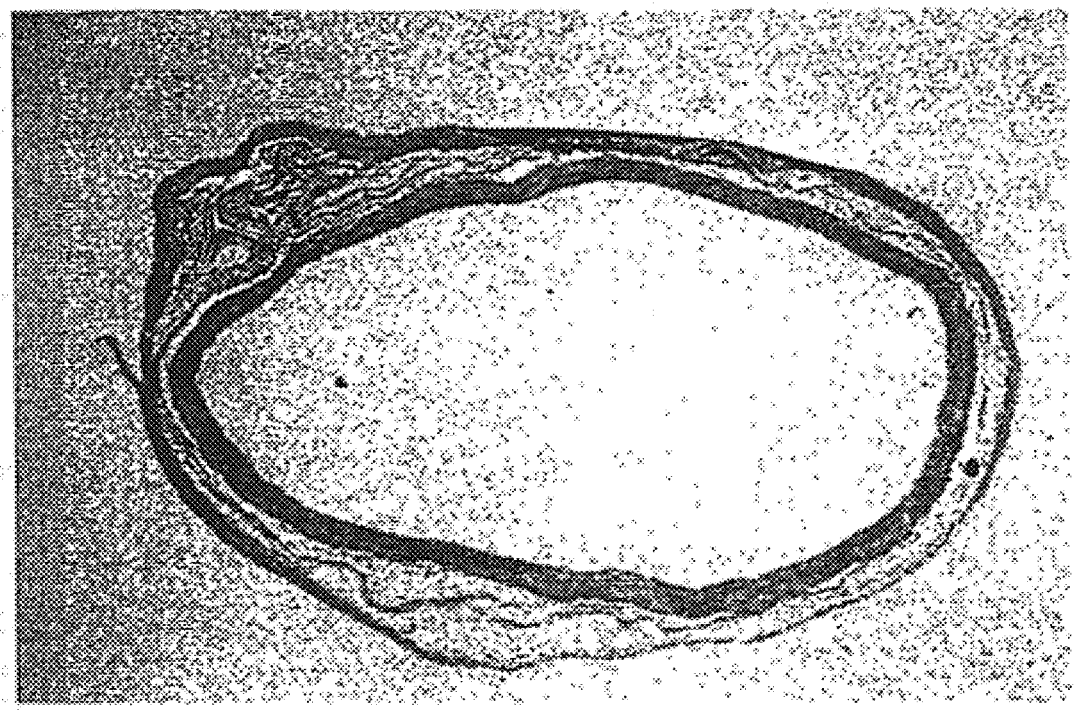
FIG. 2 is a Masson's trichrome stain (10x) a three-layer prosthesis of this invention prior to implantation.
Figure 3:
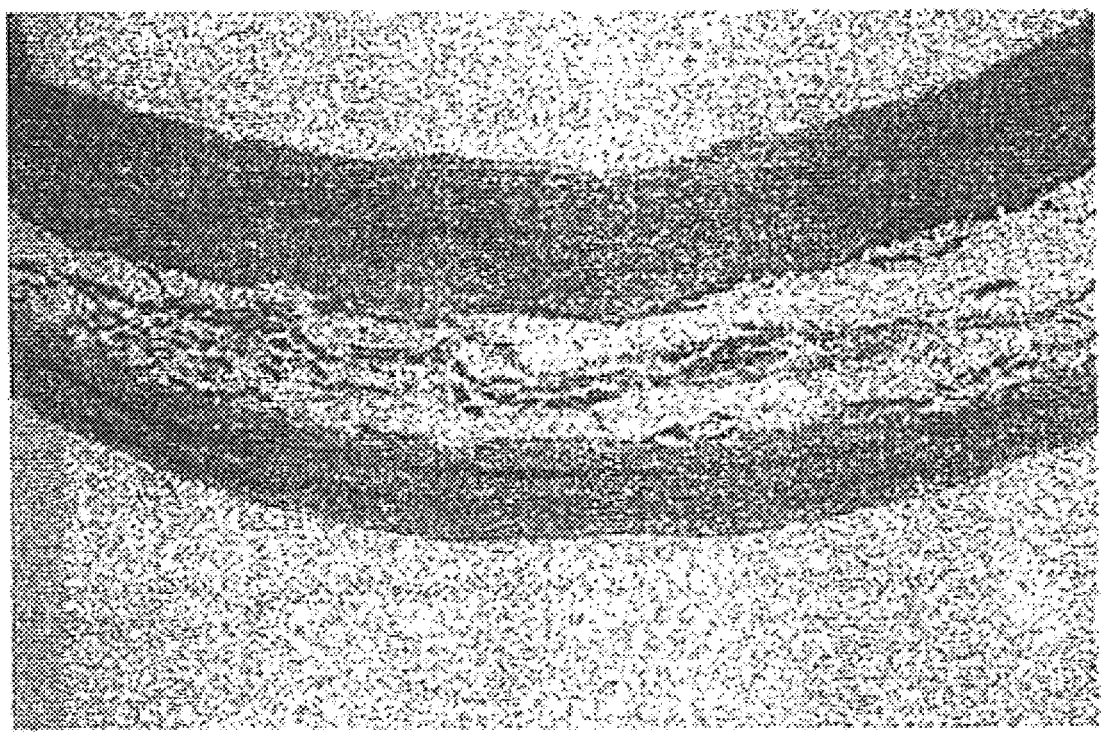
FIG. 3 is a Masson's trichrome stain (25x) a three-layer prosthesis of this invention prior to implantation.

This invention is directed to a method for treating damaged or injured organs in a patient with a bioremodelable graft, which, when implanted into a mammalian host, serves as a functioning replacement for a body part, or tissue structure, and will undergo controlled biodegradation occurring concomitantly with bioremodeling by the host's cells. In addition, the prosthesis of this invention, in its various embodiments, thus has dual properties: First, it functions as a substitute body part and second, while still functioning as a substitute body part, it functions as a bioremodeling template for the ingrowth of host cells.

When the prosthesis of this invention functions as substitute body part, it is preferably used as a vascular graft. The vascular graft prosthesis may be tubular or flat. Tubular grafts will be used as a conduit to bypass or replace arteries or veins. When formed into flat sheets, the prosthesis can be used as a vascular or intra-cardiac patch. In addition, the prosthesis can be implanted to replace diseased or damaged organs, including the esophagus, intestine, bowel, urethra, and fallopian tubes. These organs all have a basic tubular shape with an outer surface and a luminal surface. Further, the prosthesis can be used as a conduit for nerve regrowth and regeneration.

The prosthesis of this invention has increased resiliency or "spring-open" or "spring-back" properties. Spring back properties are important for applications such as a vascular tubes or patches.

The second function of the prosthesis is that of a template for bioremodeling. "Bioremodeling" is used herein to mean the production of structural collagen, vascularization, and epithelialization by the ingrowth of host cells at a rate faster than the loss of biomechanical strength of the implanted prosthesis due to biodegradation by host enzymes. The prosthesis retains the distinct characteristics of the originally implanted prosthesis while it is remodeled by the body into all, or substantially all, "self" and as such is functional as a functioning tissue structure.

The prosthesis is made of at least two layers: (a) at least one layer is composed of collagen or a collagenous material that has a smooth, uniform diameter geometry and is non-thrombogenic and (2) at least one layer which provides structural stability and biomechanical properties. The mechanical integrity means that the prosthesis is non-dilating and non-aneurysmal during bioremodeling, and additionally is pliable and suturable. The term "pliable" means good handling properties. The term "suturable" means that the mechanical properties of the layer include suture retention which permits needles and suture materials to pass through the prosthesis material at the time of suturing of the prosthesis to sections of natural vessel, a process known as anastomosis. During suturing, such vascular (blood vessel) grafts must not tear as a result of the tensile forces applied to them by the suture, nor should they tear when the suture is knotted. Suitability of vascular grafts, i.e., the ability of grafts to resist tearing while being sutured, is related to the intrinsic mechanical strength of the prosthesis material, the thickness of the graft, the tension applied to the suture, and the rate at which the knot is pulled closed.

The prosthesis of this invention is particularly directed to use as a bypass or replacement of small diameter blood vessels in the host patient. As used herein, and as is understood by those of skill in the art, a small diameter tube is less than 6 mm, typically around 3 to 4 mm. A medium diameter tube is between 6 to 12 mm. A large diameter tube is greater than 12 mm. As an example, the various vascular diameter sizes in adult humans are as follows: the diameter of aortic vessels is from about 12 to 22 mm; the diameter of the iliac vein is from 8 to 12 mm; the diameter of the superficial femoral vein is 6 mm. Above the knee, the femoral is 6 mm; across the knee, the femoral is 4 to 6 mm.

The combination of the two layers of the prosthesis of this invention when used as a tubular vascular graft work advantageously by combining a smooth thrombosis resistant flow surface on the inner (luminal) collagenous layer with the structural layer which, in addition to its other properties, aids in preventing luminal creep, that is maintaining the nominal diameter. Dilatation (or aneurysmal) failure occurs when the pulsatile pressure and forces exceed the ability of the graft to resist an increase in diameter. Dilatation or aneurysm formation is an increase in diameter beyond nominal. This occurs in both prosthesis as well as in arteriosclerotic arteries. As used herein, the term "non-dilatating" means that the biomechanical properties of the prosthesis impart durability so that the diameter of the prosthesis is not stretched, distended, or expanded beyond normal limits after implantation. As is described below, total dilatation of the implanted prosthesis of this invention is within acceptable limits. The prosthesis of this invention acquires a resistance to dilatation as a function of post-implantation cellular bioremodeling by replacement of structural collagen by host cells at a faster rate than the loss of mechanical strength of the implanted materials due from biodegradation and remodeling.

Various tubular configurations are embodied by this prosthesis as shown in FIGS. 1A, 1B, and 1C. FIG. 1A shows a two layer prosthesis with an outer collagenous layer and an inner structural layer. FIG. 1B shows a prosthesis with three layers: inner and an outer collagenous layers and a middle structural layer. FIG. 1C shows a two layer prosthesis with an inner collagenous layer and an outer structural layer.

Each of these various embodiments has applicability for particular graft replacements. The two layer prosthesis shown by FIG. 1A, with an outer collagenous layer and the inner structural layer, is useful as a replacement for vessels or hollow organs which can tolerate a less smooth inner or luminal surface, such as the esophagus, intestine, bowel, urethra, or fallopian tubes. The outer collagenous layer adds strength to the graft and allows the host's cells to attach to it, permitting ingrowth into the graft. In contrast, the prosthesis as shown in FIG. 1B and in FIG. 1C with an inner, smooth collagenous layer are useful as blood vessel replacements. The inner collagenous layer functions as a smooth flow surface.

The structural layer may be made from bioremodelable collagen or collagenous materials; or biodegradable polymeric materials, such as polylactic or polyglycolic acid, or combinations thereof; or biostable polymers, such as polytetrafluoroethylene (PTFE), polyethylene, or combinations thereof. In the preferred embodiment, collagenous material from collagenous parts of tissue from the mammalian body is used to make this layer. Such tissue includes but is not limited to intestin, fascia lata, or dura mater. The most preferred material for use as a structural layer is the tunica submucosa layer of the small intestine, termed herein the "intestinal collagen layer." As used herein, the structural layer will typically have a thickness of between about 50 microns to about 150 microns, more preferably between about 75 microns to about 125 microns. These dimensions are for an intestinal collagen layer after mechanical cleaning, but before tubulation by heat welding and crosslinking, as described below; both mechanical cleaning and heat welding significantly reduce the "apparent" thickness of the intestinal collagen layer.

When collagenous material of tissue origin is used to form the structural layer, it may be crosslinked to provide strength to the structure. Crosslinking collagenous material also provides some stiffness to the material to improve handling properties. Additionally, crosslinking collagenous material on a mandrel yields a tube of a more uniform diameter than if the material had not been crosslinked. This minimizes the risk of thrombosis which can be enhanced when there is discontinuity in the geometry of the vessel. Crosslinking agents should be selected so as to produce a biocompatible material capable of being bioremodeled by host cells. Various types of crosslinking agents are known and can be used; this is discussed below with the preferred embodiment. A preferred crosslinking agent is 1-ethyl-3-(3-dimethylaminopropyl) carbodiimide hydrochloride (EDC). There are certain crosslinking agents that cannot be used on the prosthesis of this invention since they will produce a crosslinked material that will not undergo remodeling by host cells. Glutaraldehyde, for example, is not useful for crosslinking with this invention as the residual of the glutaraldehyde monomer and lower molecular polymers are cytotoxic. Therefore, it would prevent cell ingrowth and bioremodeling.

The structural layer, at least when made with bioremodelable collagen or collagenous materials, such as the intestinal collagen layer, will be "semi-permeable," that is, permitting the ingrowth of host cells for remodeling or for deposition of the collagenous layer, as described below. Crosslinking ICL renders the material relatively less permeable as measured by water porosity testing.

The other layer of the prosthesis is the collagenous layer, the function of which is to act as a smooth flow surface for whatever its ultimate application. When used as the inner, luminal layer of the prosthesis, its function is to provide a smooth contacting surface, particularly a blood contact flow surface.

This smooth collagenous layer may be made from acid-extracted fibrillar or non-fibrillar collagen, which is predominantly type I collagen, but may also include type 3 or 4 collagen, or both. The collagen used may be derived from any number of mammalian sources, typically bovine, porcine, or ovine skin and tendons. The collagen preferably has been processed by acid extraction to result in a fibril dispersion or gel of high purity. Collagen may be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen are described, for example, in U.S. Pat. No. 5,106,949, incorporated herein by reference.

Collagen dispersions or gels for use in the present invention are generally at a concentration of about 1 to 10 mg/ml, preferably, from about 2 to 6 mg/ml, and most preferably at about 2 to 4 mg/ml and at pH of about 2 to 4. A preferred solvent for the collagen is dilute acetic acid, e.g., about 0.05 to 0.1%. Other conventional solvents for collagen may be used as long as such solvents are compatible.

Additionally, in another embodiment of the invention, the collagenous layer can include mechanically sheared or chopped collagen fibers. The chopped collagen fibers improve the spring-back performance of the collagenous layer. The chopped fibers can be added to the collagen solution used for formation of the acid-extracted collagen gel. The properties of the construct incorporating the fibers may be varied by variations in the length and diameter of the fiber; variations on the proportion of the fiber used, and partially crosslinking fibers. The length of the fibers can range from 5 cm to 5.0 cm, and will typically be incorporated into the collagen gel at a concentration of 5 to 60.

In another embodiment of the invention, the formation of the inner or outer collagenous layer can incorporate previously formed collagen threads. For example, a helix, or braid of micron diameter collagen thread could be incorporated as part of the formation of the collagen inner layer. The diameter size of the helix or braid of collagen thread can range from 25 to 50 microns, preferably 25 to 40 microns. Thus, the properties of the collagen layer can be varied by the geometry of the thread used for the reinforcement. The functionality of the design is dependent on the geometry of the braid or twist. Many of these will also effect the physical properties (i.e, compliance, radial strength, kink resistance, suture retention). Physical properties of the thread may also be varied by crosslinking.

Some portion or all of the fibers used could be polylactic acid. The physical and degradation properties of the lactic acid fibers themselves can be manipulated by varying the molecular weight, as well as the use of the D or L racemes or a mixture of D/L forms of lactic acid. Other fibers fabricated from degradable polymers could also be used, such as polyglycolic acid, caprolacatone, and polydioxinone.

Small Diameter Two-Layer Tubular Prosthesis
Method of Preparation

To further describe the prosthesis of this invention, the process of making a small diameter two layered tubular prosthesis will be described in detail below. The described two-layered prosthesis has an inner (luminal) surface composed of acid-extracted fibrillar collagen and the outer (abluminal) structural layer composed of mammalian tunica submucosa from the small intestine. Flat prosthesis can be similarly prepared with the described methods by using a flat form instead of a mandrel to produce the prosthesis.

1. Preparation of the Structural Layer.

The submucosa, or the intestinal collagen layer, from a mammalian source, typically pigs, cows, or sheep, is mechanically cleaned by squeezing the raw material between opposing rollers to remove the muscular layers (tunica muscularis) and the mucosa (tunica mucosa). The tunica submucosa of the small intestine is harder and stiffer than the surrounding tissue, and the rollers squeeze the softer components from the submucosa. As the mechanically cleaned submucosa may have some hidden, visibly nonapparent damage that affects the consistency of the mechanical properties, the submucosa may be chemically cleaned to remove substances other than collagen, for example, by soaking in buffer solutions at 4° C., without the use of any detergents such as Triton or SDS, or by soaking with NaQH or trypsin, or by other known cleaning techniques.

After cleaning, the intestinal collagen layer (ICL) should be sterilized, preferably with the use of dilute peracetic acid solutions as described in U.S. Pat. No. 5,460,962, incorporated herein by reference. Other sterilization systems for use with collagen are known in the art and can be used.

The ICL may be tubulated by various alternative means or combinations thereof. The ICL material may be formed into a tube in either the normal or the everted position, but the everted position is preferred. The tube may be made mechanically by suturing, using alternating knot stitches with suitable suture material. The knot stitch is advantageous as it allows the tube to be trimmed and shaped by the surgeon at the time of implantation without unraveling. Other processes to seam the submucosa may include adhesive bonding, such as the use of fibrin-based glues or industrial-type adhesives such as polyurethane, vinyl acetate or polyepoxy. Heat bonding techniques may also be used including heat welding or laser welding of the seam, followed by quenching, to seal the sides of the thus formed tube. Other mechanical means are possible, such as using pop rivets or staples. With these tubulation techniques, the ends of the sides may be either butt ended or overlapped. If the sides are overlapped, the seam may be trimmed once the tube is formed. In addition, these tubulation techniques are typically done on a mandrel so as to determine the desired diameter.

The thus formed structural tube can be kept on a mandrel or other suitable spindle for further processing. To control the biodegradation rates and therefore the rate of prosthesis strength decrease during bioremodeling, the prosthesis is preferably crosslinked, using a suitable crosslinking agent, such as (1-ethyl-3-(3-dimethylaminopropyl) carbodiimide hydrochloride (EDC). Crosslinking the prosthesis also aids in preventing luminal creep, in keeping the tube diameter uniform, and in increasing the burst strength. It is believed that crosslinking the intestinal collagen layer also improves the suture retention strength by improving resistance to crack propagation.

2. Deposition of Collagenous Layer(s).

Bovine collagen may be deposited on the internal surface of the submucosa as described in Example 5 of U.S. Pat. No. 5,256,418, incorporated herein by reference. Briefly, the structural intestinal collagen layer is sealed at one end by luer fittings and the collagen dispersion fills the tube. This step may also be accomplished as described in the above-referenced patent application using a hydrostatic pressure head. The inner layer of collagen can also be deposited by flowing collagen into both ends of the tube simultaneously. The tube is then placed into a bath of 20% polyethylene glycol (PEG) in isotonic phosphate buffered saline (PBS), pH about 7. The osmotic gradient between the internal collagen solution and outer PEG solution in combination cause a simultaneous concentration and deposition of the collagen along the lumen of the internal structural layer wall. The tube is then removed from the PEG bath, and a glass rod with a diameter desired diameter of the prosthesis lumen is inserted into the collagen solution. The prosthesis is then allowed to dry. The tube is then rehydrated in PBS. This process allows the collagenous layer to fill slight irregularities in the intestinal structural layer, thus resulting in a prosthesis of uniform thickness. The procedure also facilitates the bonding of the collagen gel to the intestinal collagen layer. A collagenous layer of varying thickness and density can be produced by changing the deposition conditions which can be determined by routine parameter changes. The same procedures can be used to apply the collagen to the outer surface of the submucosa to create a three-layer prosthesis.

3. Treatment of the Inner Collagenous Layer.

The prosthesis construct is thrombogenic in small diameter blood vessel replacements. It can only be used in vascular applications in high flow (large diameter) vessels. Therefore, the prosthesis must be rendered non-thrombogenic to be useful for small diameter blood vessel repair or replacement.

Heparin can be applied to the prosthesis, by a variety of well-known techniques. For illustration, heparin can be applied to the prosthesis in the following three ways. First, benzalkonium heparin (BA-Hep) solution can be applied to the prosthesis by dipping the prosthesis in the solution and then air-drying it. This procedure treats the collagen with an ionically bound BA-Hep complex. Second, EDC can be used to activate the heparin, then to covalently bond the heparin to the collagen fiber. Third, EDC can be used to activate the collagen, then covalently bond protamine to the collagen and then ionically bond heparin to the protamine. Many other heparin coating, bonding, and attachment procedures are well known in the art which could also be used.

Treatment of the inner layer with drugs in addition to heparin may be accomplished. The drugs may include for example, growth factors to promote vascularization and epitheliazation, such as macrophage derived growth factor (MDGF), platelet derived growth factor (PDGF), endothelial cell derived growth factor (ECDGF); antibiotics to fight any potential infection from the surgery implant; or nerve growth factors incorporated into the inner collagenous layer when the prosthesis is used as a conduit for nerve regeneration. The treatment of the abluminal (outer) layer may also be done in a manner similar to that for the luminal (inner) layer).

4. Cell Ingrowth Facilitation.

If the structural layer is made of ICL which is crosslinked the completed two or three layer prosthesis can be laser drilled to create micron sized pores through the completed prosthesis for aid in cell ingrowth using an excimer laser at either KrF or XeF wavelengths. The pore size can vary from 20 to 100 microns, but is preferably from about 30 to 60 microns and spacing can vary, but about 500 microns on center is preferred.

5. Sterilization.

The completed graft is then sterilized. The preferred method is to use peracetic acid as described in U.S. Pat. No. 5,460,962, incorporated herein by reference. Sterilization may also be accomplished by subjecting the prosthesis to a gamma radiation treatment ($^{60}$Co) of 10.0 to 25.0 kGy. The radiation dose eliminates all microorganisms without adversely affecting the biomechanical properties of the prosthesis.

Prosthesis Test Standards

Various tests, analysis and performance parameters have been developed over the years for vascular graft prosthesis and can be used by those of skill in the art to evaluate the prosthesis characteristics. These methods are detailed in Abbott et al., "Evaluation and performance standards for arterial prostheses,"*Journal of Vascular Surgery*, Volume 17, pages 746–756 (1993) and "American National Standard for Vascular Graft Prostheses," *American National Standards Institute* (1986).

Methods of Treating a Patient with a Prosthesis

For indications where the patient has diseased or damaged arteries or veins, replacement or bypass of a section of vessel with a vascular graft or prosthesis is necessary. An exemplary bypass procedure, a coronary artery bypass graft operation, sometimes referred to as CABG ("cabbage"), is done to reroute, or "bypass", blood around clogged arteries and improve the supply of oxygenated blood to the heart. Blood flow through these arteries is often narrowed or obstructed by accumulation of fat, cholesterol and other substances. This narrowing is termed "atherosclerosis" which can sometimes lead to a coronary arrest (heart attack).

The prosthesis of the present invention can be used to serve as a ready-to-use vascular graft for such indications that require replacement or bypass to both restore physical function and eventually, because of its bioremodelable characteristics, its biological function.

In the situation of a coronary bypass, the heart is made accessible by opening the body cavity. The vascular prosthesis is attached at one end to the aorta and the other end to the coronary artery below the blocked area. In the situation of a vessel replacement, the vessel is made accessible and is ligated at two points located at either end of the section to be replaced so as to prevent the flow of blood through the section. The prosthesis is engrafted at or near the points where the original vessel is removed.

Surgical placement of the graft, in both the bypass and replacement situations, can be accomplished in either of two ways. An interpositional placement of the graft is end-to-end anastomosis wherein the section of vessel is completely severed and one end of the graft is sutured to the end of the vessel. End-to-side anastomosis, commonly done in bypass procedures, is when an incision is made in the sidewall of the vessel to create an opening and one end of the graft is sutured to the opening. The placement of the ends of the graft may be both end-to-end, both end-to-side or a combination of the two techniques.

Once both ends of the graft are sutured in place, blood flow is resumed and monitored as the graft functions as a prosthetic blood vessel. Further, as the prosthesis of the present invention is bioremodelable, it functions as a remodeling template for the ingrowth of host cells. Over time, the graft is replaced with the patient's cells which, at the same time, degrade the graft and replace it with new matrix so that it becomes a new tissue structure.

The following examples further describe the materials and methods used in carrying out the invention. The examples are not intended to limit the invention in any manner.

EXAMPLES

Example 1

Two and Three Layer Tubular Prosthesis

The small intestine of a pig was harvested and mechanically stripped so that the tunica submucosa is delaminated from the tunica muscularis and the luminal portion of the tunica mucosa of the section of small intestine. (The machine was a striper, crusher machine for the mechanical removal of the mucosa and muscularis layers from the submucosal layers using a combination of mechanical action (crushing) and washing using hot water.) This was accomplished by running the intact intestine through a series of rollers that strip away successive layers. The intestinal layer was machine cleaned so that the submucosa layer solely remains. The submucosa was decontaminated or sterilized with 0.1% peracetic acid for 18 hours at 4° C. and then washed after the peracetic acid treatment.

This machine cleaned intestinal collagen layer (ICL) was mounted and stretched on a frame so that it was under slight tension both radially and longitudinally. Coarse running basting stitches (6-0 Novafil®) were applied to form a small diameter tube, with the submucosa in the everted position. The stretched ICL tissue was cut in half to overlap and form flaps. A fine seam through both layers of ICL was formed using 6-0 Novafil® suture with an alternating knot stitch so that a final internal diameter of 4.5 mm was obtained. The flaps were then removed. The small-diameter ICL tube, used as the structural layer, was placed onto a 4.5 mm glass rod and crosslinked with 100 mmol EDC (Pierce) for 18 hours at room temperature.

The machine cleaned intestinal collagen layer (ICL) in a fully hydrated condition was mounted and wrapped on a mandrel so that the ends overlapped. The ICL wrapped mandrel was heated to 62° C. plus or minus 10° C. for 15 minutes in a moist atmosphere, followed by quenching at 4° C. in iced aqueous solution for 5 minutes. The tubulated ICL was then crosslinked with EDC for 6 to 18 hours, rinsed, and removed from the mandrel.

Polycarbonate barbs (luer lock fittings that are funnel shaped on one end) were placed tightly in either end of the tube and then the tube was placed horizontally in a deposition fixture. A 15 ml reservoir of 2.5 mg/ml acid-extracted fibrillar collagen, termed "dense fibrillar collagen" ("DFC") (U.S. Pat. No. 5,256,418, incorporated herein by reference) with a hydrostatic pressure head of 150 mmHg (for 5 feet) was attached via the barbs. (The pressure will depend on the height of the collagen reservoir.) The collagen was allowed to fill the lumen of the ICL tube and was then placed into a stirring bath of 20% MW 8000 polyethylene glycol (Sigma Chemical Co.) for 16 hours at 4° C. The apparatus was thee dismantled. To fix the luminal diameter, a 4 mm diameter glass rod was placed into the collagen-filled ICL tube. The prosthesis was then allowed to dry for 18 hours at 4° C.

A layer of acid extracted fibrillar collagen was deposited onto a 4.0 mm diameter porous ceramic mandrel as described in Example 4, U.S. Pat. No. 5,256,418, incorporated herein by reference, for 6 hours and dehydrated at 4° C.

The ICL tube, as described above, was placed over the dried collagen and a second layer of dense fibrillar collagen (DFC), as described above, was applied for 18 hours to the outside (abluminal) of the ICL.

Pores were drilled in the ICL/DFC or the DFC/ICL/DFC using an excimer laser at either KrF or XeF wavelengths. The pore size was about 50 microns and spacing was 500 microns on center.

The construct was rehydrated in 4° C. 1M PBS for 6 hours. The prosthesis was treated with application of benzalkonium heparin in isopropranol. Sterilization was accomplished with 0.1% peracetic acid for 18 hours at 4° C.

The prosthesis was packaged and sterilized with 10.0 to 25.0 kGy of gamma radiation ($^{60}$Co). (The prosthesis can also be shipped dry and rehydrated in saline, prior to implantation.)

Example 2

Remodeling of the Collagen Graft

Long Term Implant Histology

Three-layer prosthesis were implanted in the infra-renal aorta of rabbits using standard surgical techniques. Proline, 7-0, was used to construct end to end anastomoses to the adjacent arteries. The grafts were 1.5 cm in length and 3 mm in diameter. No anti-platelet medications were administered post-operatively.

Following pressure perfusion with McDowells-Trump fixative, the grafts were explanted, and submitted for light and electron microscopy. Specimens from 30, 60, 90, 120, and 180 day implants were available. Materials were examined with H/E, VonGieson elastica, Masson's Trichrome, g-Actin, Factor VIII, and Ram-11 (macrophage) stains, and polarized microscopy. Qualitative morphometric comparisons were made to stained non-implanted retention samples.

Histological evaluations demonstrated that the graft was readily invaded by host cells. The luminal collagen was resorbed and remodeled with the production of new collagen by host myofibroblasts. The ICL was readily invaded, re-populated by host cells, and remodeled. Endothelial cells were demonstrated on the lumninal surface of the prosthesis.

At 30 days, large numbers of mononuclear inflammatory cells were seen on both the luminal and abluminal surfaces of the collagen. Modest numbers of Ram-11 positively staining macrophages, were observed. At the surface of the cast collagen, there was cell mediated collagen resporption and remodeling. There was minimal loss of the collagen bulk at this time.

At 60 days, the cellular response was more myofibroblastic than inflammatory. Significant amounts of new collagen as well as small amounts of elastin were readily identified. About 50 percent of the cast collagen had been remodeled. Endothelial cells as identified by SEM appearance, TEM (Weibel-Palade bodies) and positive Factor VIII staining, covered the surface of the remodeling construct.

At 90 days, the matrix surrounding the myofibroblasts (as identified with g-actin) stained prominently for collagen.

The cytoplasm of cells themselves had reduced amounts of cytoplasm as compared to previous timepoints.

At 120 days, the stroma demonstrated well organized predominantly radially and longitudinally oriented myofibroblasts and host produced collagen. Significant amounts of elastin could be identified. Greater than 90 percent of the implanted collagen had been remodeled. No Ram-11 staining macrophages were identified.

At 180 days, cells and the matrix of the neo-artery were quite mature. The cells were small with minimal cytoplasm. The collagen was dense and distinctly radially and longitudinally oriented.

There was no histological evidence of an immune response to either the luminal collagen layer or the abluminal ICL layer. No grafts became dilated or aneurysmal.

Example 3

Comparison of Three-Layer Prosthesis and e-PTFE

Both two-layer and three-layer small diameter prosthesis were implanted and evaluated over time for patency and remodeling.

FIGS. 4–9 show the results of a comparison of three-layer prothesis with a similarly configured contra-lateral reference material, e-PTFE, in a canine femoral artery study. The grafts were implanted in canines as femoral interposition prosthesis. Grafts were explanted from 30 to 256 days.

Histological evaluation of the three-layer collagen graft demonstrated cellular ingrowth into the graft at 30 days, with more than 90 percent of the graft collagen remodeled by 90 days; and a mature 'neo-artery' at 180 days. Host tissue bridged the anastomosis by 60 days with the anastomosis only demarcated by the non-resorbable sutures. The predominant cell type in the neo-artery was a positive g-Actin staining smooth muscle like cell. The surface of the remodeled graft was lined by endothelial cells as demonstrated by SEM, TEM and Factor VIII staining.

In contrast, at times to 256 days, no ingrowth into the e-PTFE artery was observed either across the anastomosis or along the body of the graft. Only a thin smooth muscle cell hyperplastic response was demonstrated extending from the adjacent artery a short distance on the graft's luminal surface. The graft was encapsulated by mature fibrous tissue with no evidence of cellular or tissue extension into the graft.

Figure 4:
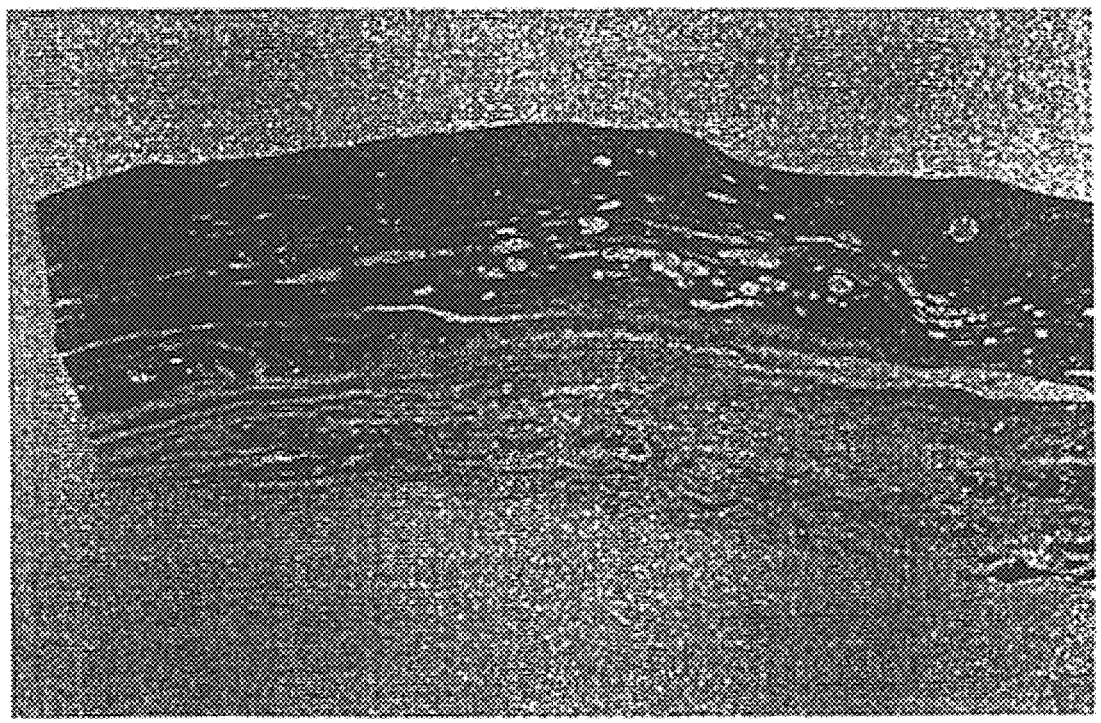
FIG. 4 is a Masson's trichrome stain (10x) of the proximal anastomosis of a a three-layer prosthesis of this invention implanted as a canine femoral interposition prosthesis (256 days).
Figure 5:
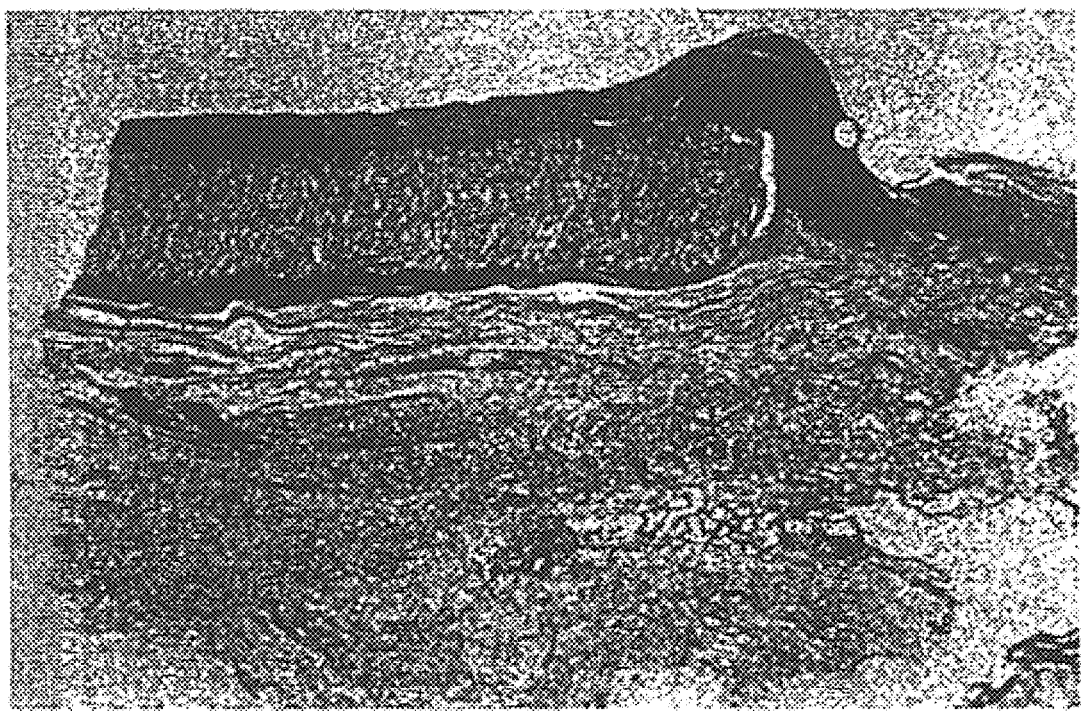
FIG. 5 is a Masson's trichrome stain (10x) of the proximal anastomosis of an e-PTFE graft implanted as a canine femoral interposition prosthesis (256 days).
Figure 6:
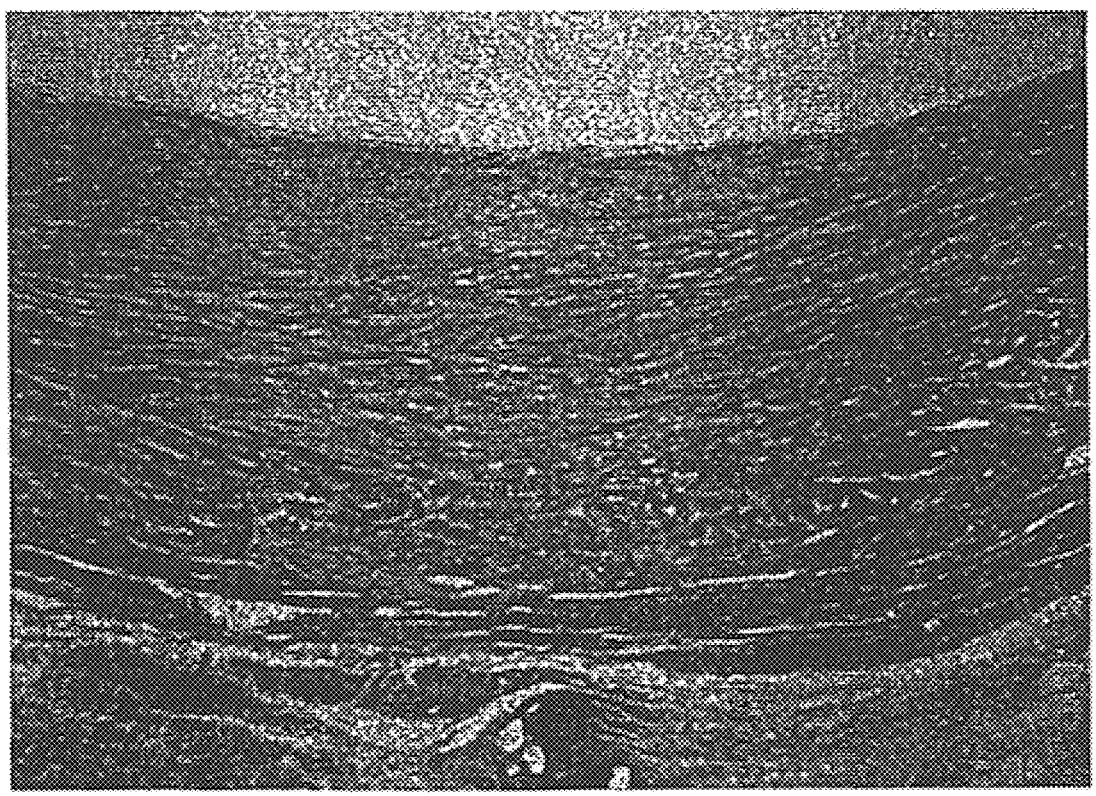
FIG. 6 is a Masson's trichrome stain (25x) of the proximal anastomosis of a three-layer prosthesis of this invention implanted as a canine femoral interposition prosthesis (256 days).
Figure 7:
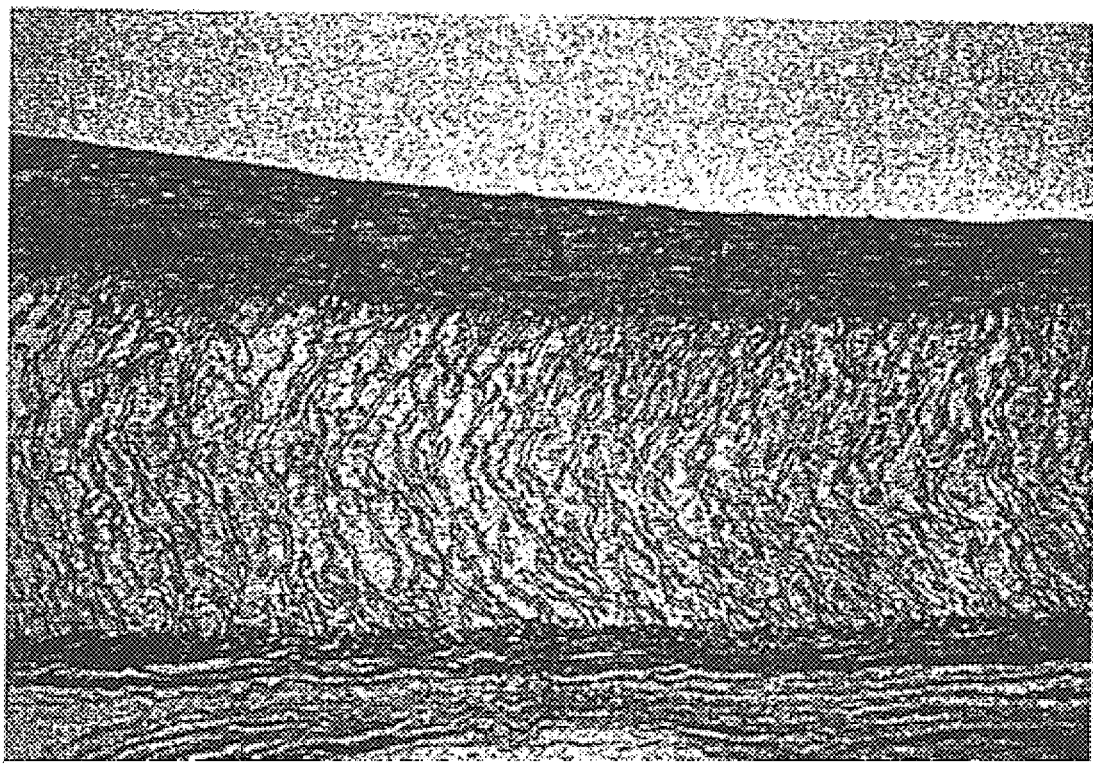
FIG. 7 is a Masson's trichrome stain (25x) of the proximal anastomosis of an e-PTFE graft implanted as a canine femoral interposition prosthesis (256 days).

FIG. 4 is a Masson's trichrome stain (10×) of the proximal anastomosis of the three-layer prosthesis at 256 days compared with FIG. 5 of an e-PTFE graft. FIG. 6 is also a Masson's trichrome stain at 25× of the proximal anastomosis of a three-layer prosthesis at 256 days compared with FIG. 7 of an e-PTFE graft.

Figure 8:
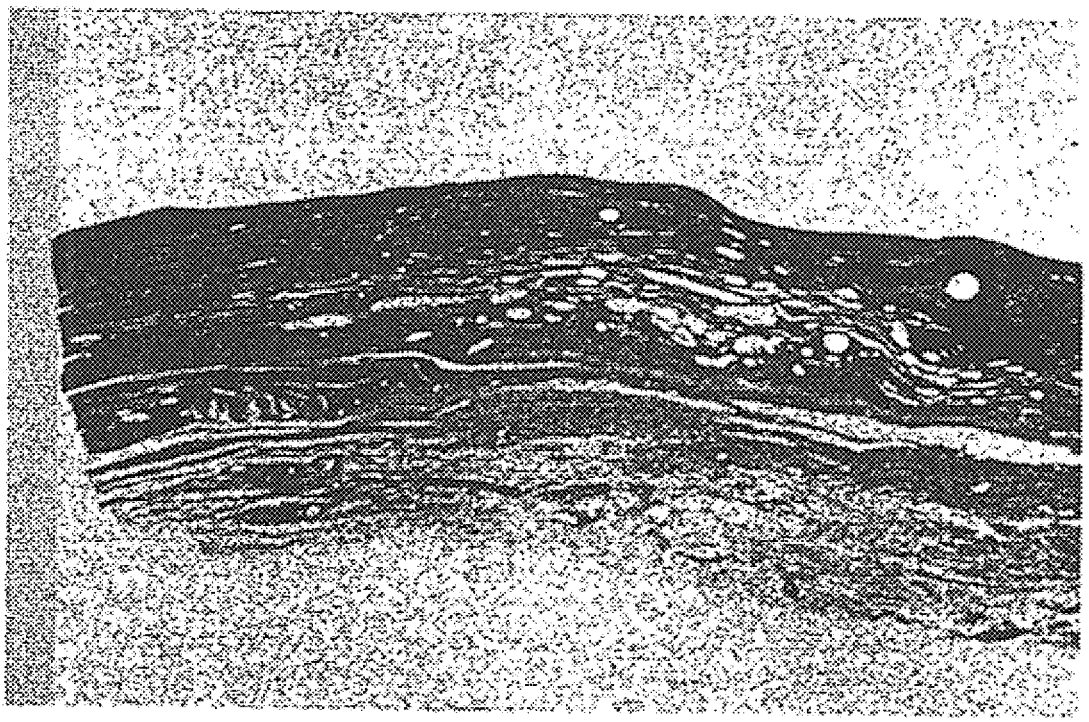
FIG. 8 is a Verhoeff's elastic stain (10x) of the proximal anastomosis of a three-layer prosthesis of this invention implanted as a canine femoral interposition prosthesis (256 days).
Figure 9:
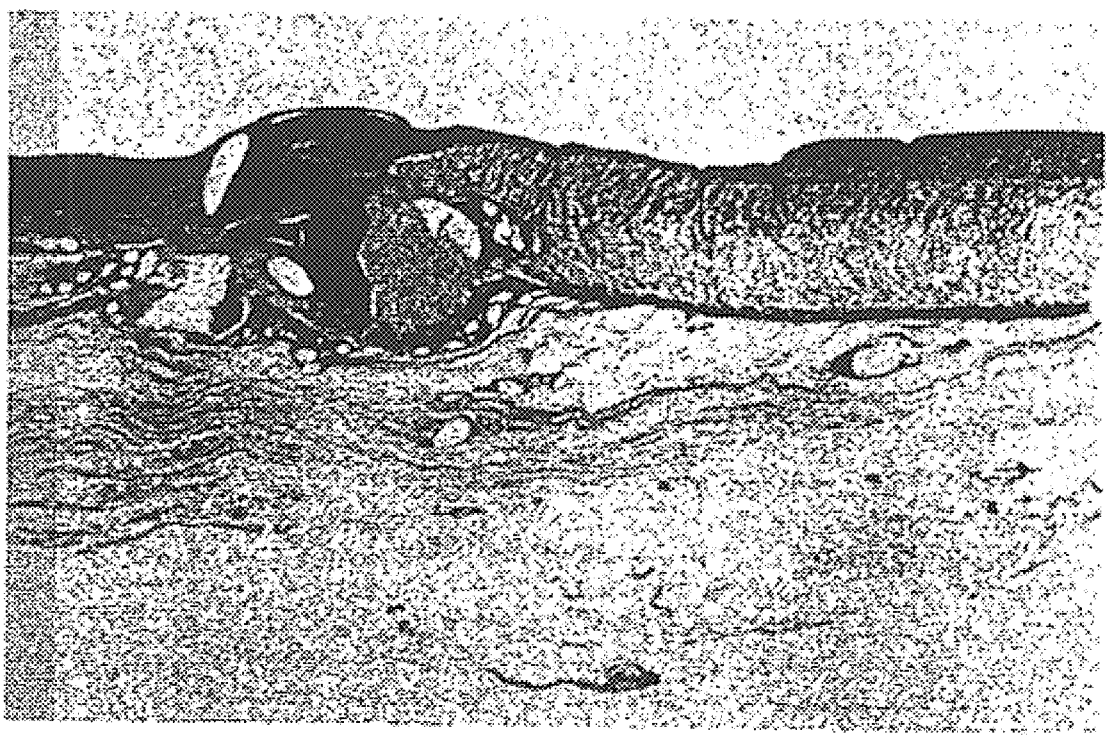
FIG. 9 is a Verhoeff's elastic stain (10x) of the proximal anastomosis of an e-PTFE graft implanted as a canine femoral interposition prosthesis (256 days).

FIG. 8 is a Verhoeff's elastic stain (10×) of the proximal anastomosis of a three-layer prosthesis implanted as a canine femoral interposition prosthesis at 256 days compared with FIG. 9 of an e-PTFE graft.

Although the foregoing invention has been described in some detail by way of illustration and example for purposes of clarity of understanding, it will be obvious to one skilled in the art that certain changes and modifications may be practiced within the scope of the invention, as limited only by the scope of the appended claims.

We claim:

1. A bioremodelable prosthesis for treating a patient with a diseased or damaged organ, comprising a first layer that contains acid-extracted fibrillar or non-fibrillar collagen, and a second layer derived from the tunica submucosa of the small intestine that provides structural stability, is pliable, and is semi-permeable, wherein said prosthesis all undergoes controlled biodegradation occurring with adequate living cell replacement such that the original prosthesis is replaced by the patient's living cells.

2. The prosthesis of claim 1, wherein the prosthesis is tubular and the diseased or damaged organ is an artery or a vein.

3. The prosthesis of claim 2, wherein the tubular prosthesis has a diameter of less than 6 mm.

4. The prosthesis of claim 2, wherein the tubular prosthesis has a diameter of between 6 to 12 mm.

5. The prosthesis of claim 2, wherein the tubular prosthesis has a diameter of greater than 12 mm.

6. The prosthesis of claim 1, wherein the diseased or damaged organ is the esophagus, intestine, bowel, urethra, or fallopian tubes.

7. The prosthesis of claim 1, wherein said first layer has a smooth flow surface.

8. The prosthesis of claim 7, wherein the smooth flow surface is thrombosis-resistant.

9. The prosthesis of claim 1, wherein said second layer is crosslinked.

10. The prosthesis of claim 9, wherein said second layer is crosslinked with 1-ethyl-3-(3-dimethylaminopropyl) carbodiimide hydrochloride (EDC).

11. The prosthesis of claim 1, wherein said second layer has a thickness of between about 50 microns to about 150 microns.

12. The prosthesis of claim 1, wherein the tunica submucosa of the small intestine is mechanically cleaned to remove the tunica muscularis and the tunica mucosa.

13. The prosthesis of claim 12, wherein said mechanically cleaned tunica submucosa is chemically cleaned.

14. The prosthesis of claim 1, wherein the tunica submucosa of the small intestine is sterilized.

15. The prosthesis of claim 1, wherein said prosthesis further comprises a third layer.

16. The prosthesis of claim 1, wherein the first layer is on the inside of the prosthesis.

17. The prosthesis of claim 1, wherein the second layer is on the inside of the prosthesis.

18. The prosthesis of claim 1, wherein the prosthesis is treated with a drug.

19. The prosthesis of claim 1, wherein the first layer is treated with a drug.

20. The prosthesis of claim 1, wherein the second layer is treated with a drug.

21. The prosthesis of claim 18, 19, or 20, wherein the drug is heparin.

22. The prosthesis of claim 18, 19, or 20, wherein the drug is a growth factor.

* * * * *